United States Patent
Simmons et al.

(10) Patent No.: US 9,189,601 B2
(45) Date of Patent: Nov. 17, 2015

(54) APPARATUS, SYSTEM, AND METHOD FOR ACCURATE DISPENSING OF PRESCRIPTION MEDICATIONS

(75) Inventors: George T. Simmons, Paradise Valley, AZ (US); Sara Sprague, Orlando, FL (US)

(73) Assignee: JIREH HEALTH, LLC, Scottsdale, AZ (US)

(*) Notice: Subject to any disclaimer, the term of this patent is extended or adjusted under 35 U.S.C. 154(b) by 208 days.

(21) Appl. No.: 13/601,997

(22) Filed: Aug. 31, 2012

(65) Prior Publication Data
US 2013/0238119 A1 Sep. 12, 2013

Related U.S. Application Data

(63) Continuation-in-part of application No. 13/047,531, filed on Mar. 14, 2011, now abandoned.

(60) Provisional application No. 61/314,522, filed on Mar. 16, 2010.

(51) Int. Cl.
A61J 7/04 (2006.01)
G06F 19/00 (2011.01)
A61J 7/00 (2006.01)

(52) U.S. Cl.
CPC ........... *G06F 19/3462* (2013.01); *A61J 7/0084* (2013.01); *A61J 7/0481* (2013.01); *A61J 1/1418* (2015.05); *A61J 7/0445* (2015.05); *A61J 2200/30* (2013.01)

(58) Field of Classification Search
CPC . A61J 7/0481; G07F 17/0092; G06F 19/3462
USPC .................. 700/237, 240, 241, 244
See application file for complete search history.

(56) References Cited

U.S. PATENT DOCUMENTS

| | | | |
|---|---|---|---|
| 5,710,551 A * | 1/1998 | Ridgeway | 340/870.09 |
| 6,102,855 A * | 8/2000 | Kehr et al. | 600/300 |
| 6,449,218 B1 * | 9/2002 | Lluch | 368/10 |
| 6,471,087 B1 * | 10/2002 | Shusterman | 221/2 |
| 6,644,496 B1 * | 11/2003 | Ambrosio | 221/2 |
| 7,048,141 B2 * | 5/2006 | Abdulhay et al. | 221/3 |
| 7,344,047 B2 * | 3/2008 | Gilmore | 221/2 |
| 7,689,318 B2 * | 3/2010 | Draper | 700/236 |
| 7,783,379 B2 * | 8/2010 | Beane et al. | 700/237 |
| 7,996,105 B2 * | 8/2011 | Handfield et al. | 700/237 |
| 8,417,381 B2 * | 4/2013 | Vonk et al. | 700/244 |
| 8,600,548 B2 * | 12/2013 | Bossi et al. | 700/240 |
| 8,700,212 B1 * | 4/2014 | Bruno et al. | 700/242 |
| 2002/0149472 A1 * | 10/2002 | Roe | 340/309.15 |
| 2006/0161435 A1 * | 7/2006 | Atef et al. | G06F 21/31 704/246 |

* cited by examiner

*Primary Examiner* — Timothy Waggoner
(74) *Attorney, Agent, or Firm* — Polsinelli PC (57) ABSTRACT

An apparatus for the recording and dispensing of medication has an electronic device having a screen and a base electronic unit with a space designed to allow insertion of a cassette housing medication to be dispensed. A first input device is coupled to the electronic device to send data to the electronic device to verify a particular user of the electronic device. A dispensing device is coupled to the electronic device for dispensing medication to the particular user once the electronic device has verified the particular user.

20 Claims, 7 Drawing Sheets

APPARATUS, SYSTEM, AND METHOD FOR ACCURATE DISPENSING OF PRESCRIPTION MEDICATIONS

CROSS-REFERENCE TO RELATED APPLICATIONS

This is a continuation-in-part application that claims benefit to U.S. patent application Ser. No. 13/047,531, filed on Mar. 14, 2011, which claims benefit to U.S. Provisional Patent Application Ser. No. 61/314,522 filed on Mar. 16, 2010, which are herein incorporated by reference in theft entirety.

TECHNICAL FIELD

The present disclosure describes medical dispensing systems, and in particular, apparatuses, methods, and systems for controlling access to prescribed medication as well as the monitoring, tracking, recording, communicating and reporting the dispensing of prescribed medication to patients for compliance purposes.

BACKGROUND

Securing access to, and thereby ensuring accuracy in the dispensing, monitoring and tracking of prescription medications, addresses a significant medical and health cost concern, as does assuring the timely recording and communicating the administering of medication to the patient. According to the World Health Organization, each year the improper dispensing of prescribed medications results in harm to approximately 1.5 million people. This has led to significant medical costs in treating such patients. For example, in the year 2000 alone, such errors resulted in nearly $1 billion in added medical costs. Also, in the HHS and CMS Report of 2006, it was stated that over $170 billion was paid out by insurance carriers for unnecessary and/or wasted prescription medications in the United States.

It has been found that many patients do not comply with proper usage of prescription medications for a variety of reasons. In some instances, it may be a consequence of a patient knowingly taking medication for which that patient does not have a prescription, and which, for example, may instead have been prescribed to another patient. In other instances, a patient may inadvertently take too much or too little medication, as a consequence of not clearly understanding the dosing instructions or because of forgetfulness or confusion. Improper usage of prescribed medications can also occur as a consequence of a patient not realizing a risk of a harmful interaction with another medication being taken at the same time by the patient, or by a patient continuing to take a medication without realizing that he or she is experiencing a harmful side effect.

SUMMARY

One aspect of the present disclosure includes a system for dispensing prescribed medication. The system includes a remote server comprising a database including patient information for a plurality of patients. The system also includes a dispensing apparatus in operative association with the remote server, a dispensing device in operative association with the dispensing apparatus for dispensing medication, and an input device for receiving an identification input from the patient. The dispensing apparatus includes at least one processor to receive the identification input from the input device to verify that the patient of a plurality of patients is authorized to access the dispensing device and provide such access when the identification input of the patient is verified.

Aspects of the present disclosure also include a system for dispensing medication. The system includes a remote server comprising a database including patient information for a plurality of patients. The system also includes a dispensing apparatus in operative association with the remote server, a dispensing device for dispensing medication, and an input device for receiving an identification input from a patient authorized to access the prescribed medications. The electronic device includes at least one processor to receive the identification input from the input device to verify that a patient of the plurality of patients is authorized to access the dispensing device and provide such access to the prescribed medications when the patient is verified. At least one processor is configured to provide access to the dispensing device when the patient is verified and dispense medication from the dispensing device to the patient according to a prescribed schedule. In addition, at least one processor is configured to generate a dispensing transaction when medication is dispensed from the dispensing device.

Aspects of the present disclosure also include methods for dispensing medication. These methods may include receiving, at at least one processor, identification input of a patient from an input device to verify that the patient of a plurality of patients is authorized to access prescribed medications stored in a dispensing device. The method further includes providing, at the at least one processor, access to the dispensing device when the identification input from a patient is verified. The method further includes generating, at the at least one processor, a dispensing transaction when medication is dispensed from the dispensing device.

BRIEF DESCRIPTION OF THE FIGURES

Aspects of the present disclosure may be better understood and its numerous objects, features, and advantages made apparent to those skilled in the art by referencing the accompanying drawings. It should be understood that these drawings depict only typical embodiments of the present disclosure and, therefore, are not to be considered limiting in scope.

DETAILED DESCRIPTION

Aspects of the present disclosure relate to apparatuses, systems, and methods for securing outpatient access to prescribed medication and the automated reporting of medication compliance. In various aspects, identification input for a particular patient may be received and subsequently analyzed to allow access to prescribed medications. Once medication is accessed, a transaction may be recorded and provided for analysis by authorized parties.

Figure 1:
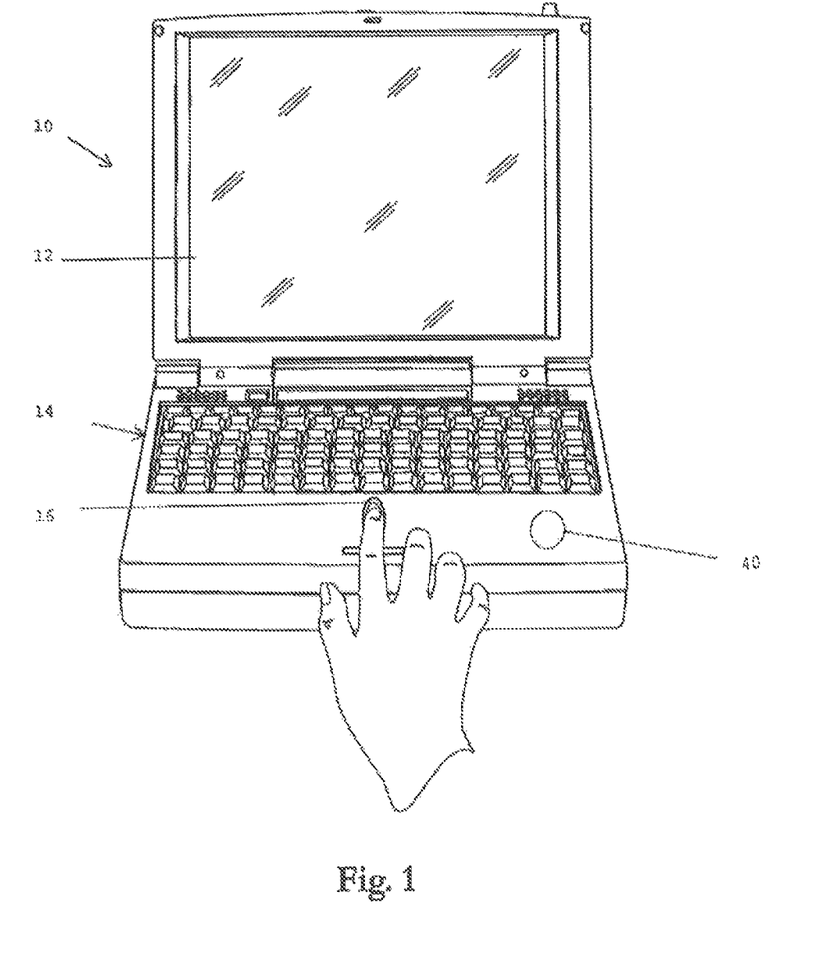
FIG. 1 is a perspective view of a personalized dispensing apparatus consistent with an embodiment of the present invention.
Figure 2:
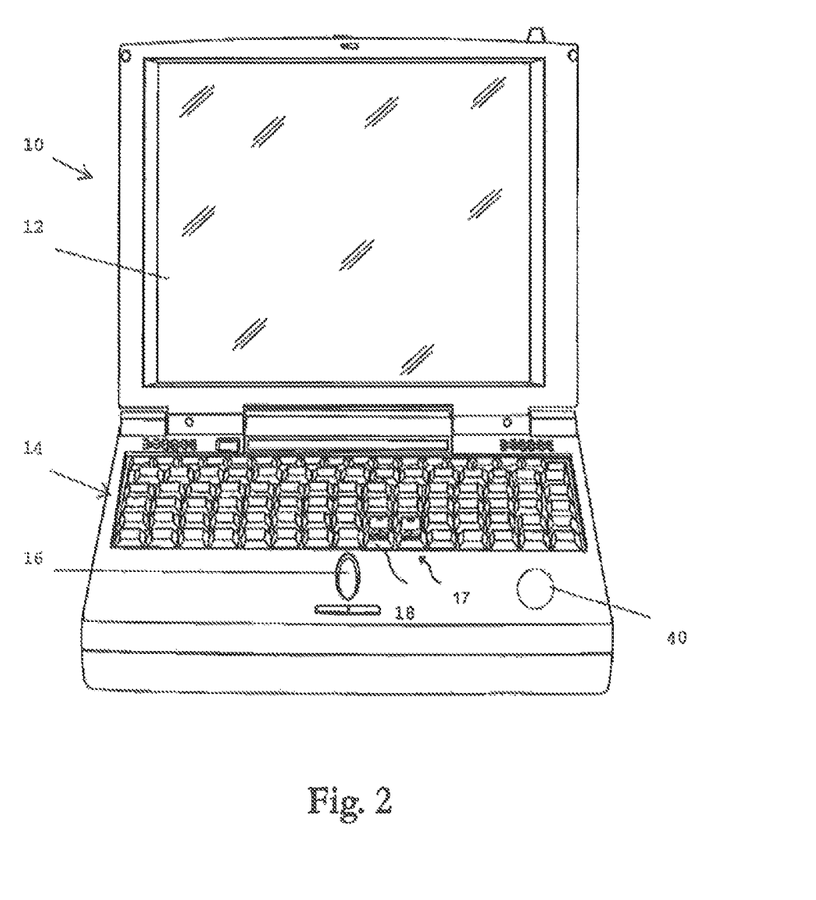
FIG. 2 is a perspective view of the personalized dispensing system apparatus of FIG. 1, with two "bubbles" housing medications shown in an open position.
Figure 3:
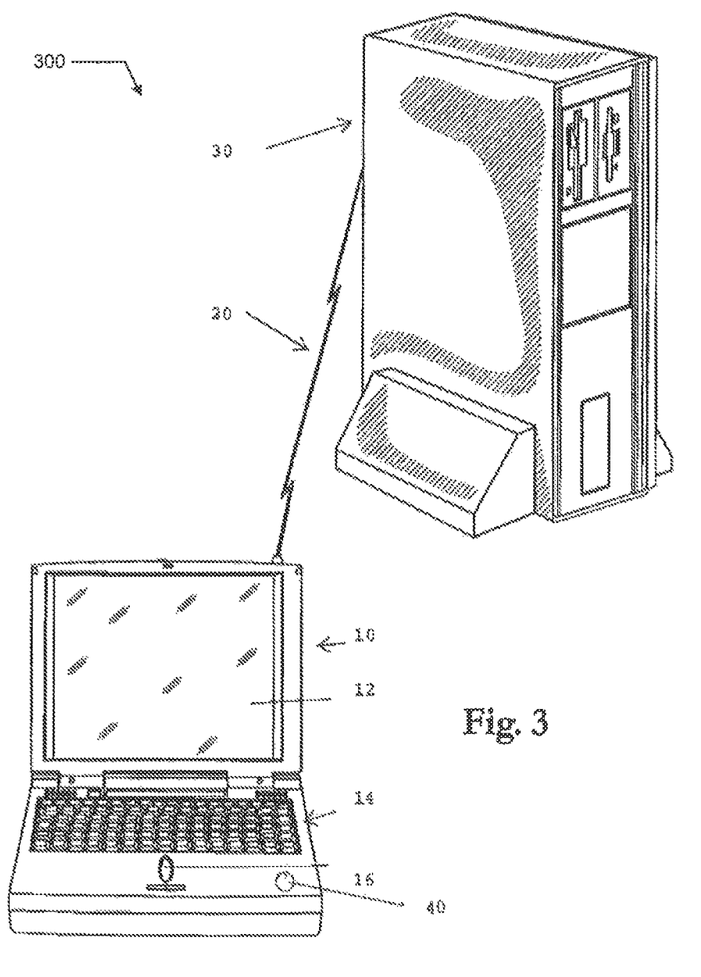
FIG. 3 is a perspective view of a dispensing system consistent with an embodiment of the present invention, illustrating communication between a personalized dispensing apparatus and a server.

Referring to FIGS. 1-2, an embodiment of a dispensing apparatus 10 consistent with an embodiment of the present invention is shown. The dispensing apparatus 10 may be an electronic device, apparatus, gadget, appliance, etc., capable of securely dispensing prescribed medications to a patient. For example, in one embodiment, the personalized dispensing apparatus 10 may have a visual appearance similar to a laptop computer, including a screen 12 and a housing area to securely store and dispense prescribed medication 14. The dispensing apparatus 10 may incorporate computer hardware and software, and may be incorporated or otherwise included in a computing system 300 for dispensing prescribed medication 14, as illustrated in FIG. 3. For example, system 300 may enable a user to receive data or instructions from the dispensing apparatus 10, which may be resident in the dispensing apparatus 10 or downloaded to the dispensing apparatus 10 from a remote server, thereby allowing data to be displayed on the screen 12; storing data in internal memory; and allowing the dispensing apparatus 10 to in turn upload data over a network or the like with one or more various external computing devices, such as a remote server.

The dispensing apparatus 10 may further include at least one input device, such as a biometric security device 16 and/or other input security device, such as a keypad to provide secure access to the prescribed medication 14 stored in the dispensing apparatus 10. In the embodiment shown in FIGS. 1-2, the biometric security device 16 may be a fingerprint recognition pad that the patient slides the finger across, which captures the individual's fingerprint for comparison against stored fingerprints authorized to access the prescribed medication 14. Alternatively or in addition, the biometric security device 16 may be an iris scanner, a voice or face recognition device, or the like. In one embodiment, the biometric security device 16 may be an RFID reader or the like, capable of reading a chip located on the user's body (e.g., on a bracelet) or under the user's skin for permitting access to the prescribed medication 14. The goal of the biometric security device 16 is to provide assurance that an individual accessing prescribed medication contained within the dispensing apparatus 10 has proper authority to have the prescribed medication dispensed to that individual, for example because the individual has a prescription for that medication or is an authorized health care worker involved in dispensing the prescribed medications to a particular individual for which the dispensed medication is intended.

The dispensing apparatus 10 may include at least one dispensing device 17, for example, in the form of a plurality of dispensing bubbles 18, which are adapted to store and dispense a prescribed medication to an authorized patient. As noted above, access to the interior of the dispensing bubbles 18 may be controlled by the biometric security device 16, so that only a patient or pre-approved, authorized caregiver may access the interior of the dispensing bubbles 18, as regulated by software resident in the dispensing apparatus 10. Access by a licensed pharmacist or equivalent licensed health care professional may be permitted for loading the dispensing bubbles 18 with a prescribed medication to be dispensed, or for dispensing of prescribed medication. Upon verification by the dispensing apparatus 10, through the biometric security device 16, that an individual is authorized to access and dispense the prescribed medication, the dispensing apparatus 10 may permit an opening/unlocking/unsealing operation of the dispensing bubble or location(s) 18. The dispensing bubbles or location(s) 18 may have the visual aspect of a computer key, as shown by way of example in FIG. 2, or may have a different visual aspect, as desired. The substrate beneath the dispensing bubbles 18 may also define enclosed cavities of varying size and configuration to accommodate different dosages and/or multiple prescribed medications to be administered at the same time.

Figure 2B:
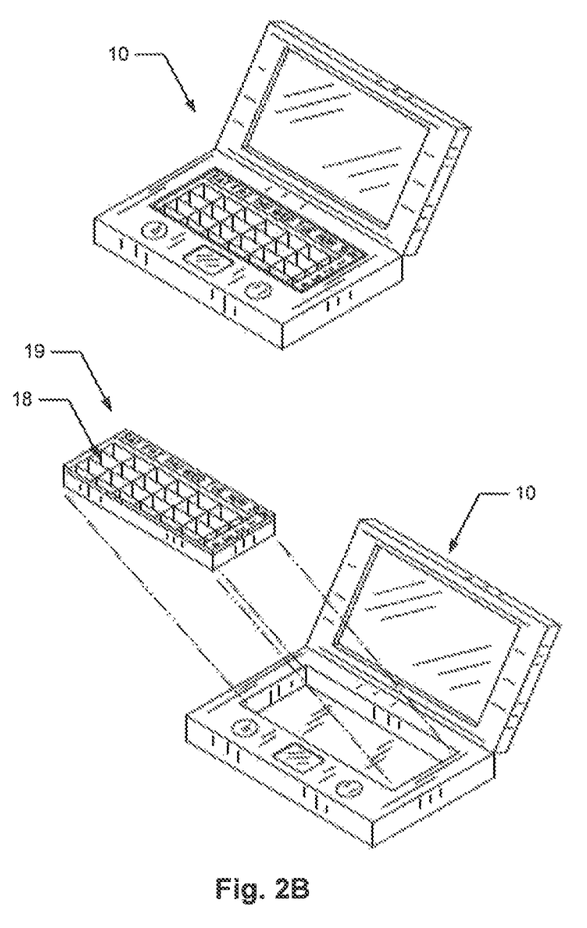
FIG. 2B is a perspective view of a modular cassette apparatus of FIG. 1, consistent with an embodiment of the present invention.

In some embodiments, the dispensing apparatus 10 may include a dispensing device 17 in the form of a modular cassette 19, which may be removable from the dispensing apparatus 10 to allow for separate loading and delivery of the prescribed medication 14 without transferring out the balance of the dispensing apparatus 10, such as its various other hardware components to accomplish this operation. Such a configuration provides for an individual, such as a patient, to remain in control of the hardware and software for the dispensing apparatus 10, thereby minimizing the chances of damage, misuse and the potential for compromising patient data contained in the dispensing apparatus 10.

FIG. 2B is an example illustration of the modular dispensing cassette 19. The modular cassette 19 may include a plurality of compartments, each compartment being configured for store a single piece or portion of prescribed medication 14 to be dispensed. The specific size and shape of the modular dispensing cassette 19 may vary according to the size and arrangement of the individual compartments capable of storing prescribed medication 14. For example, each compartment may only be capable of holding a single dosage of medication prescribed to a particular patient. Alternatively, each compartment may be capable of holding or otherwise storing multiple dosages of medication prescribed to a patient. In one particular embodiment, the compartments within the modular dispensing cassette 19 may be arranged in a row of seven compartments, each compartment representing a single day of a seven day week. Alternatively, the compartments may be arranged in other ways, such as according to meal times for a week, etc. It is contemplated that the compartments may be arranged in accordance with any type of medical prescription parameter.

The modular dispensing cassette 19 may be inserted and/or otherwise operatively connected to the dispensing apparatus 10. In particular, the modular dispensing cassette 19 may attach to and/or be placed in operable communication with the various hardware/software components of the dispensing apparatus 10. For example, in one embodiment, the modular dispensing cassette 19 may be electronically locked and/or released from the dispensing apparatus 10. Specifically, the dispensing apparatus 10 may contain electronic terminals which match/connect to similar contact points on the modular dispensing cassette 19. The contact points allow for electrical signals, programmatically generated by the various hardware and/or software components of the dispensing apparatus 10 to lock the modular dispensing cassette 19 into the base unit of the dispensing apparatus 10 for the purpose of dispensing prescribed medication 14 and release the modular dispensing cassette 19 from the base unit of the dispensing apparatus 10 for the purpose of allowing the modular dispensing cassette 19 to be taken to a pharmacy to be refilled with prescribed medication 14. In each such embodiment, the space allocated for the cassette housing the prescribed medication 14 may be different in shape, size of compartments and overall capacity.

Additionally, the modular dispensing cassette 19 may also contain electrical wiring and/or contacts for connecting to and operatively interfacing with the electronic circuitry and/or various other hardware and/or software components of the dispensing apparatus 10.

Various software applications, functions, modules, and/or processes, etc., as will be described in more detail below, may be resident on the dispensing apparatus 10 to regulate access by a user to the dispensing bubbles/compartments 18 and/or the modular dispensing cassette 19. When the dispensing bubbles/compartments 18 and/or the modular dispensing cassette 19 is loaded, the pharmacist or other authorized fulfillment person may input information into the dispensing apparatus 10 relating to the particular medication being loaded therein. Such inputting may include dosing information or, alternatively, dosing information generally suitable for a particular prescribed medication 14 may be pre-loaded.

At the time of loading, it may further be desired to input into the prescribed dispensing apparatus 10 information concerning the patient for whom the prescribed medication is intended. Such information may include information identifying a particular patient and any corresponding information describing the medical characteristics of the patient, such as information about the patient's medical history, identity, and perhaps contact information for a health care provider, insurance information, and the like (collectively referred to herein as "Patient Information"). In one embodiment, the dispensing apparatus 10 may include a card reader or other such reader device, permitting a health plan card or the like containing relevant health data and/or Patient Information relating to the patient to be read by the dispensing apparatus 10, including for example information regarding the prescribed medication(s) and dosage, thus facilitating a substantially automated entry into the dispensing apparatus 10 of the patients relevant health data and/or Patient Information and eliminating the need for a pharmacist to enter such information manually. The health plan card may also be used by the health care worker to gain authorized access to the dispensing apparatus 10. Additionally, the card may be used to create a security match with the biometric data input on the dispensing apparatus 10 at the time of access.

In one embodiment, as will be described in more detail below, the software applications, functions, modules, and/or processes on the dispensing apparatus 10 may include various functions, some of which may include a clock and calendar function that enables the triggering of alerts and/or windows of scheduled access times when a patient is required to take a medication located in a dispensing bubble 18. Such an alert may come in the form of an audible sound produced by the dispensing apparatus 10, a visual alert displayed on the screen 12, a text message or email generated by the dispensing apparatus 10, some combination thereof, or the like. The alert may include, in addition to the reminder to take the prescribed medication 14, information regarding side effects, the name of the prescribing doctor, an image of the medication, and/or other useful information. Upon receiving an alert and/or by reason of matching the date and time information with the biometric input data, a user may then access the prescribed medication by activating the biometric security device 16 and triggering an opening of the suitable dispensing bubble 18 or various compartments of the modular cassette 19. The opening of each bubble/compartment 18 is facilitated by programmatically sending electrical signals from the base unit circuitry of the dispensing apparatus 10 to wiring contacts incorporated on the modular dispensing cassette 19, which are located to allow such opening function. In one embodiment, an alert may continue until the dispensing apparatus 10 determines that the patient has accessed the prescribed medication 14 as described herein.

Upon removal by the user of the prescribed medication 14 from the dispensing bubble 18 and/or in another embodiment the various compartments of the modular dispensing cassette 19, the software applications, functions, modules, and/or processes resident on the dispensing apparatus 10 may record that the requisite dose of the prescribed medication 14 was dispensed, and may schedule an alert for the next dose. In one embodiment, an individual will not be permitted access to the dispensing bubble 18 or the various compartments of the modular dispensing cassette 19, even if the individual is the patient to whom the stored medication has been prescribed, if it is not yet time for the next dose, so as to prevent overmedication.

Referring again to FIG. 2, in accordance with one embodiment, the dispensing apparatus 10 may have another input device 40. The input device 40 may be built into the dispensing apparatus 10. Alternatively, the input device 40 may be attached to an I/O port of the dispensing apparatus 10. The I/O port may be a USB port, a FireWire port, or the like. The listing of the above is given as an example and should not be seen as to limit the scope of the present invention. The input device 40 may be used to check the blood, saliva, or the like, of the individual. Alternatively, the input device 40 may be used to read a biometric chip implanted in the individual. Thus, an individual may provide blood, saliva, or the like to the input device 40 or the input device 40 may read a biometric chip or it may accept test data read from another device, such as a blood pressure monitor. The dispensing apparatus 10 may be loaded with software to analyze the specimen placed in the input device 40, or read the information from the biometric chip or another input device. The software may analyze whether the user has taken the medication and/or the results of having taken the prescribed medication. Data generated from the inclusion of such ancillary bio feedback may be recorded in the input device 40 and communicated to the patient's EHR or other data base in a remote server for additional analysis and user interrogation.

Figure 4:
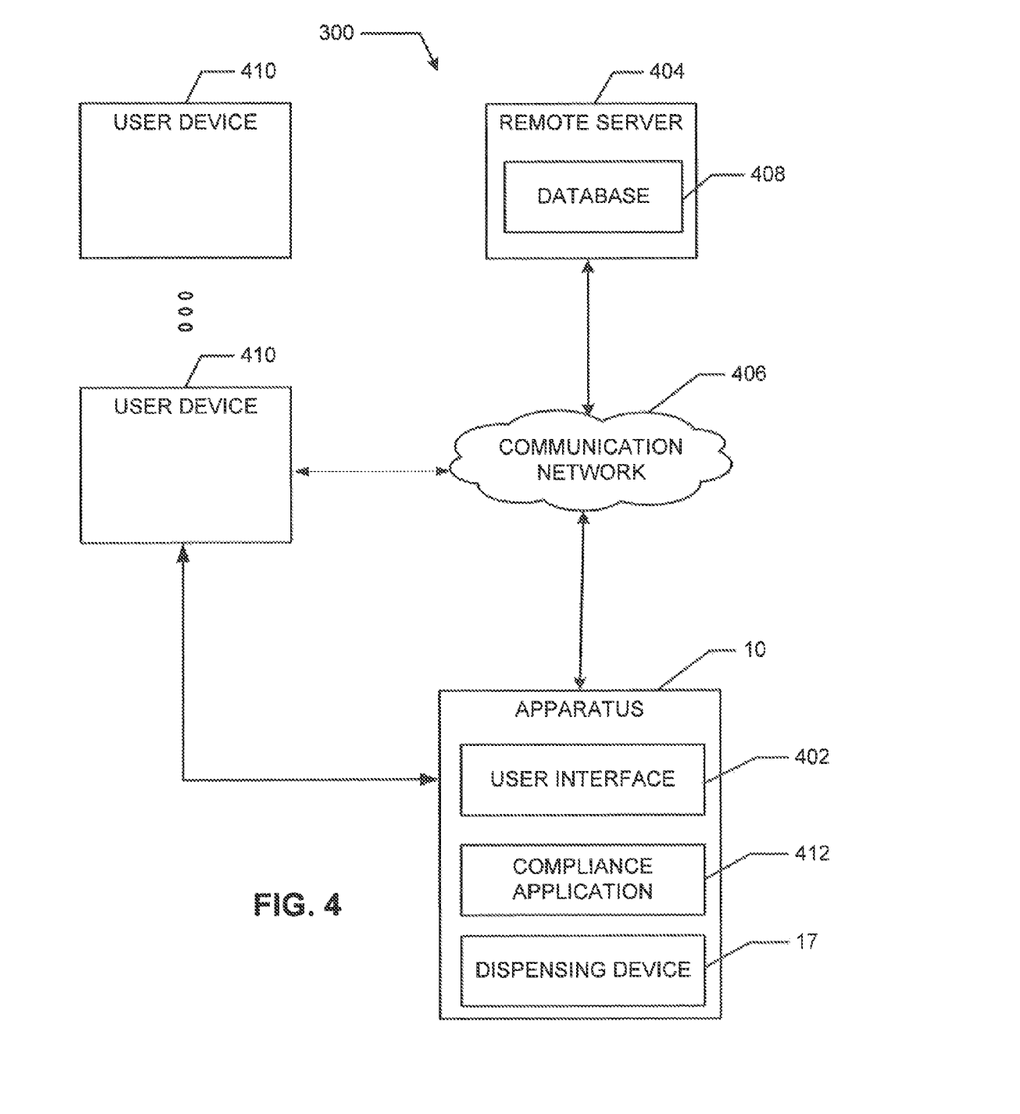
FIG. 4 is another illustration of a computing environment for dispensing medications in accordance with one aspect of the present disclosure.

FIG. 4 illustrates another embodiment of the computing environment 300 in which the dispensing apparatus 10 may be used to monitor the dispensing of the prescribed medications to patients for compliance purposes. The computing environment 400 includes the dispensing apparatus 10, which in addition to the various components described above in conjunction with FIG. 1 (e.g. dispensing device 17), may include one or more processors and/or processing systems that process software or other machine-readable instructions and may include a memory to store the software or other machine-readable instructions and data. The memory may include volatile and/or non-volatile memory. Additionally, the dispensing apparatus 10 may include a communications system to communicate via a wireline and/or wireless communications, such as through the Internet, an intranet, an Ethernet network, a wireline network, a wireless network, a mobile communications network, and/or another communications network. The dispensing apparatus 10 may include a user-interface (UI) 402 for an individual to provide input and may include a display (not shown) such as a computer monitor, liquid crystal display, for viewing data and/or input forms, and any combination of input/output devices (not shown), such as a keyboard, or a pointing device (e.g., a mouse, trackball, pen, or touch pad), speaker, and/or any other type of device for receiving input.

In some embodiments, the dispensing apparatus 10 may communicate with a remote server 404 using a communications network 406 to receive Patient Information, health data, and/or any other information related to the prescribed medication for a patient. For example, the dispensing apparatus 10 may transmit requests to the remote server 404 through the communications network 406 for Patient Information that may be used to verify medication prescription compliance for a particular patient. In response, the remote server 404 may provide a response to the dispensing apparatus 10 with the requested information.

The communications network 406 may include the Internet, an intranet, a local area network, a wireless local network, a wide area network, or another communications network, as well as combinations of such networks. In one particular embodiment, the dispensing apparatus 10 may access the remote server 404 and its various computing resources using a cloud computing architecture in which the computing resources of the remote server 404 are provided as a service over a network, such as the communications network 406. FIG. 3 is an alternative illustrative example of the dispensing apparatus 10 communicating with the remote server 404 (i.e., via the communications network 406).

In some embodiments, the remote server 404 may be a personal computer, work station, server, mobile device, mobile phone, tablet device, processor, and/or other processing device, which may be field programmable. The remote server 404 may include software and one or more processors that process software or other machine-readable instructions. For example, the remote server 404 may include software capable of performing various analytical comparison functions for comparing and/or analyzing Patient Information and/or electronic health records ("EHR"), as will be described in detail below.

For example, any prior non-compliant transactions may be automatically accumulated by the remote server 404 with the present transaction to indicate the number and frequency of non-compliance for the patient in a pre-selected time period. It may also be determined and reported that previous episodes of non-compliance by the patient led to ER visits or hospital admittances. As another example, EHRs on the remote sever 404 may be accessed by authorized users for the purpose of monitoring individual patient compliance or to determine compliance for a class, grouping or category of patients. For example, for a given patient, the most recent one of few compliance transactions recorded may be interrogated to determine any possible need for intervention by a physician, caregiver, pharmacy, other providing agency or the insuring entity; any prior non-compliant transactions may be automatically accumulated with the present transaction to indicate the number and frequency of non-compliance for the patient in a pre-selected time period. It may also be determined and reported by the remote sever 404 that previous episodes of non-compliance by the patient led to ER visits or hospital admittances. In addition to these examples, there may be a menu of report generator format and content options for the user to compile a variety of comparative information on one or more patients.

The remote sever 404 may include a memory to store the software or other machine-readable instructions and data. The memory may include volatile and/or non-volatile memory. Additionally, the remote server 404 may also include a communications system to communicate via a wireline and/or wireless communications, such as through the Internet, an intranet, an Ethernet network, a wireline network, a wireless network, a mobile communications network, and/or another communication network, such as communications network 406. The remote server 404 may include a database and/or data store 408 containing Patient Information corresponding to a plurality of patients, their prescribed medications, their health care providers, and the like. In one embodiment, the dispensing apparatus 10 may communicate with the remote server 404 and may, for example, query the database 408 for updated information regarding potential undesirable interactions with other prescribed medications—including medication prescribed after the patient first received a prescription for the stored medication—or side effects, perhaps taking into account more current information regarding a patients medical condition. In another embodiment, the dispensing apparatus 10 may communicate with the remote server 404 to store information regarding a user's dispensing of the prescribed medication. For example, in one embodiment, the remote server 404 and/or the database 408 may include EHRs for one or more patients. Each EHR may contain various types of patient identifiers (medical and otherwise), insurance carriers, health parameters, health history, existing allergies, attending physicians, past and present prescribed medications, dosages, dispensing schedules and medication compliance history; these EHR formats may be layered fields menu driven for efficient data access and sorting.

The information, such as Patient Information, stored at the remote server 404, may be made accessible to the user's health care provider, insurance provider, pharmacy, clinic, hospital, and/or any other individual or entity with authorized access to such data or to data on a class of patients taking certain medications, whether by allowing the health care provider and/or others referenced above to access the database 408 or by transmitting the data to a processing device, such as user device(s) 410, which may be a personal computer, work station, server, mobile device, mobile phone, tablet device, processor, and/or other processing device operated by or on behalf of the provider of such parties.

The remote server 404 may send, transmit, or otherwise provide information including Patient Information, health data, etc., received by the remote server 404 from the dispensing apparatus 10 through the communications network 406. Subsequently, the dispensing apparatus 10 may execute a compliance application 412 that processes such data to monitor and/or control the dispensing of prescribed medication to patients and/or to verify patient compliance.

Figure 5:
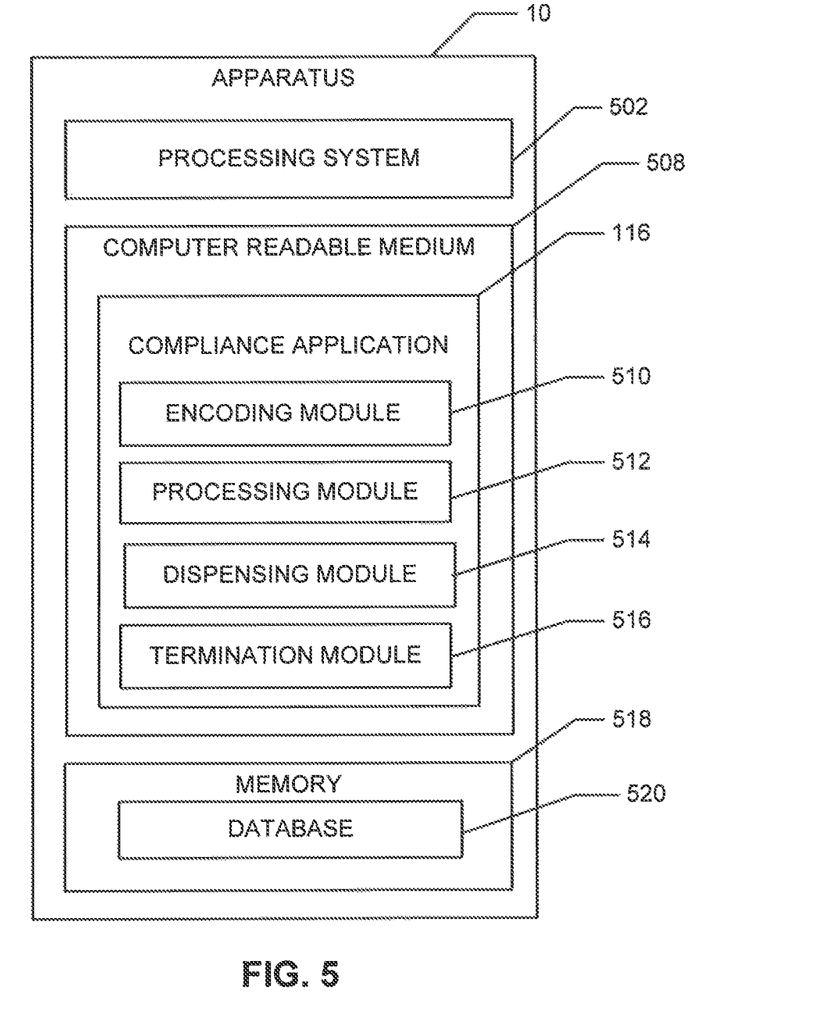
FIG. 5 is a block diagram of a patient device in accordance with one aspect of the present disclosure.

FIG. 5 is an example block diagram illustrating various computing components of the dispensing apparatus 10 according to one embodiment of the present disclosure. As illustrated, the dispensing apparatus 10 may include a processing system 502 to initiate and/or otherwise facilitate the dispensing of prescribed medication 14 to patients and verify the patient's compliance. The processing system 502 may be in operative communication with a memory 518. The memory 518 may include volatile and/or non-volatile memory, and may provide a database 520 to store data. The database 520 may be a general repository of data including, but not limited to, medical data, prescription data, Patient Information, biometric information, and/or any other information that may correspond to patients and/or be used to dispense medicine to patients. The database 520 may include memory and one or more processors or processing systems to receive, process, query and transmit communications and store and retrieve data. In another aspect, the database 520 may be a database server.

The dispensing apparatus 10 may include a computer readable medium ("CRM") 508, which may include computer storage media, communication media, and/or another available computer-readable medium that may store executable instructions to implement the compliance application 116 and/or associated functions, processes, etc. CRM 508 may include non-transient computer storage media and communication media. By way of example and not limitation, computer storage media includes memory, volatile media, non-volatile media, removable media, and/or non-removable media implemented in a method or technology for storage of information, such as machine/computer-readable/executable instructions, data structures, program modules, or other data. Communication media includes machine/computer-readable/executable instructions, data structures, program modules, or other data. Generally, program modules include routines, programs, instructions, objects, components, data structures, etc., that perform particular tasks or implement particular abstract data types. For example, as illustrated, in some embodiments CRM 508 may include or otherwise store an encoding module 510, a processing module 512, a dispensing module 514, and a termination module 516 of the compliance application 116. In some embodiments, other modules may also be included.

Referring to FIGS. 1-6, in one particular embodiment, the dispensing apparatus 10 may launch, run, execute, interpret, or otherwise perform the logical instructions and/or processes of the compliance application 116. For example, a process 600 depicts an exemplary method and/or process for monitoring the dispensing of prescribed medication to a patient to verify compliance. Process 600 executes instructions in which Patient Information for one or more patients is received at operation 602. As illustrated in FIG. 5, an encoding module 510 receives patient information corresponding to one or more patients. As described above, Patient Information may include information identifying a patient and any corresponding information describing the medical characteristics of the patient, such as, but not limited to, name, residence, insurance information, medical history, medical condition, prescription information, etc. In one particular embodiment, the Patient Information may also include a biometric profile corresponding to the particular patient. A biometric profile describes the various biometric characteristics and/or traits corresponding to a particular patient that may be used to uniquely identify the patient authorized to access the prescribed medication 14, such as fingerprints and/or fingerprint data, voice, gait, Iris data, etc. Any Patient Information received by the encoding module 510 may be encoded and stored in the database 520. For example, a biometric profile (i.e., Patient Information) corresponding to a particular patient may be received from the remote server 404 and subsequently stored in the database 520 of the dispensing apparatus 10. As another example, any biometric profiles for a particular patient may be stored within the EHR corresponding to the patient. In yet another example, a biometric profile may be converted into a digitized file for use in matching biometric input for access to the medication. The specific type of encoding may be determined by the type(s) of biometric algorithms employed. Biometric algorithms are automated methods that enable a biometric system to recognize an individual by his or her biometric characteristics. Typically, biometric characteristics consist of a sequence of automated operations performed by the system to verify or identify its ownership. Such operations may include quality assessment, enhancement, feature extraction, classification/indexing, matching and fusion, etc.

In one particular embodiment, the Patient Information received by the encoding module 510 may include one or more instructions describing how a particular patient may access medication(s). For example, the encoding module 510 may receive one or more "prescribed schedules" describing how the identified patient should access medication(s). Each prescribed schedule may describe various rules, guidelines, instructions, and/or policies under which medications may be dispensed to the patient. Each prescribed schedule may articulate specific times, dates, frequencies, etc., for which the identified patient may access and consume medications dispensed by the dispensing apparatus 10. For example, a prescribed schedule may indicate that a particular patient "Tom S." is required to be dispensed prescribed medication once a week on Mondays, between 1:00 PM and 2:00 PM. In one particular embodiment, the prescribed schedule may be a test file capable of being parsed. Alternatively, in another embodiment, the prescribed schedule may be a data structure stored on the dispensing apparatus 10 that may be queried. In yet another embodiment, the prescribed schedule may be defined as an elapsed-time calculation defined from the last dispensing transaction to the next.

Identification input may be received to identify a particular patient at operation 604. As illustrated in FIG. 5, a processing module 512 may receive the identification input and subsequently process, parse, and/or analyze the input to identify a particular patient. The identification input may include various pieces of information that may be matched and/or otherwise cross-referenced with the Patient Information stored on the dispensing apparatus 10 to identify the particular patient. For example, the processing module 512 may receive identification input including biometric data, such as a fingerprint from the biometric security device 16, and process the fingerprint to identify a particular patient by comparing the fingerprint to one or more of the biometric profiles stored in the database 520.

In one embodiment, the identification input may include a PIN number, which may be used to initiate an override capability. The override capability may provide access to the dispensing apparatus 10 when attempting to access the dispensing apparatus 10 via biometric input fails. Specifically, identification input may be provided in the form of a PIN number, or any unique identifier to the dispensing apparatus 10. Subsequently, the processing module 512 may process the PIN number to provide override access to the dispensing apparatus 10. The dispensing apparatus 10 may report the malfunction of the biometric access, such as to the remote server 404, and require repair of the feature within some prescribed time frame. If such features were not repaired, the processing module 512 may cause the dispensing apparatus 10 to self lock until such repair was made.

Figure 6:
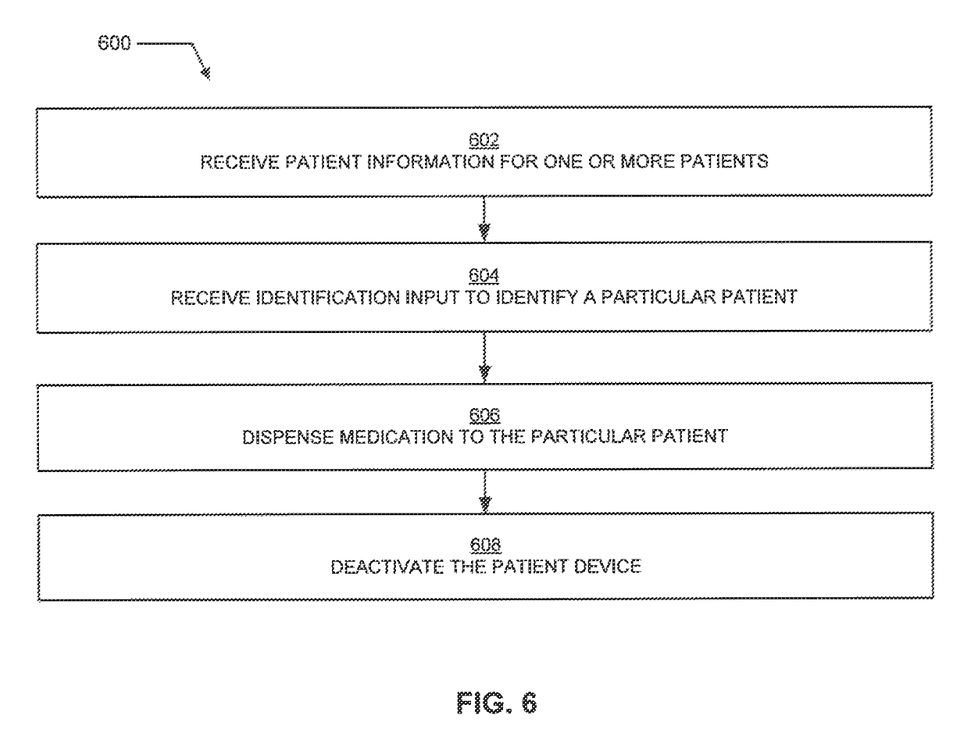
FIG. 6 is an example process for providing an adaptive interface in accordance with one aspect of the present disclosure.

Once a particular patient has been identified, one or more prescribed medications may be dispensed at operation 606. In particular, a dispensing module 514 may dispense or otherwise initiate the dispensing of prescribed medication from the dispensing apparatus 10 to the identified patient. Initially, the dispensing module 514 may access any instructions, such as a prescribed schedule, corresponding to the identified patient. Subsequently, the dispensing module 514 may initiate and/or otherwise activate the dispensing mechanism of the dispensing apparatus 10 to dispense prescribed medication to the identified patient according to the instructions and/or prescribed schedule for the patient.

The dispensing module 514 may activate, initiate and/or otherwise trigger various components of the dispensing apparatus 10 when the dispensing apparatus 10 is required to dispense prescribed medication. Additionally, the dispensing module 514 may generate various alerts during the dispensing of prescribed medication that provide an indication to the patient that medication may be dispensed. The alert may be an audible alert, a visual alert, a text message and/or email, or some combination thereof. In conjunction with the alert, the dispensing module 514 may provide or otherwise include in the alert information regarding side effects of the medication being dispensed, the name of the doctor prescribing the prescribed medication 14, an image of the prescribed medication, and/or other medical information, etc.

When prescribed medication is dispensed from the dispensing apparatus 10, the dispensing module 514 may record and/or store a "dispensing transaction" in the database 520 and/or elsewhere. The dispensing transaction may describe the or otherwise indicate that medication was dispensed from the dispensing apparatus 10, and may also include corresponding information, such as the time the medication was dispensed, the amount of medication dispensed, etc. In one particular embodiment, each dispensing transaction may be transmitted to and/or otherwise communicated to the remote server 404. Once received by the remote server 404, software on the remote may be initiated to set flags on patient records to alert users to non-compliant behavior; however, because of the wide ranging parameters for determining severity of individual non-compliance, the user is best suited to determine same from preset expectations, patient history and specific/individualized analytical results.

Once the prescribed medication prescribed to the particular patient has been depleted, or the dispensing apparatus 10 can no longer dispense medications, the dispensing apparatus 10 may be automatically deactivated at operation 608. As illustrated in FIG. 5, a termination module 516 may shut down, turn off, and/or deactivate the patient device and subsequently communicate to the remote server 404 that the device has been deactivated. Additionally, similar to the dispensing module 514, the termination module 516 may generate various alerts for display indicating that a patient should have the medication(s) refilled. Any alerts generated may be transmitted to the prescribing doctor(s) and the insurance entity. Once the patient device has been deactivated, the termination module 516 may initiate the dispensing apparatus 10 to release the prescribed medication 14 container from the electronic locking mechanism, such that another container filled with prescribed medication may be inserted.

The description above includes example systems, methods, techniques, instruction sequences, and/or computer program products that embody techniques of the present disclosure. However, it is understood that the described disclosure may be practiced without these specific details. It should be noted that the present invention may have application outside the field of health care, where controlled dispensing of an item only to an authorized recipient may be desired.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

While embodiments of the disclosure have been described in terms of various specific embodiments, those skilled in the art will recognize that the embodiments of the disclosure can be practiced with modifications within the spirit and scope of the claims.

The described disclosure may be provided as a computer program product, or software, that may include a machine-readable medium having stored thereon instructions, which may be used to program a computer system (or other electronic devices or components, such as FPGAs designed for remote programming) to perform a process according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

The invention claimed is:

1. A system for dispensing of medication comprising:
a remote server comprising a database, the database comprising patient information for a plurality of patients; and
a dispensing apparatus in operative association with the remote server, the dispensing apparatus including a dispensing device in operative association with the dispensing apparatus for dispensing medication, a first input device for receiving an identification input from a patient, and at least one processor to
receive identification input from the first input device to verify that the patient of the plurality of patients is authorized to access the medication stored in the dispensing device;
in response to the verification,
obtain a first prescribed schedule from a plurality of prescribed schedules stored in the database, the first prescribed schedule corresponding to the patient, the first prescribed schedule defining personalized instructions for dispensing the medication to the patient and wherein the personalized instructions includes at least one instruction defining how frequently the patient should consume the medications;
provide access to the medication and to the dispensing device when the patient is verified based in part on the at least one instruction; and
analyze bio feedback results of the patient having taken the medication as received from a second input device including reading biomedical information via a biometric chip implanted in the patient;
wherein the first input device is capable of reading the biometric chip for verifying whether the patient of the plurality of patients is authorized to access the medication stored in the dispensing device, wherein the dispensing device comprises a modular cassette comprising a plurality of locked compartments for storing prescribed medication of the patient; and wherein the dispensing apparatus includes a screen portion and a housing portion extending orthogonally with respect to the screen portion and the dispensing device is disposed within a top side of the housing portion.

2. The system of claim 1, wherein the at least one processor is further configured to receive the patient information corresponding to the plurality of patients via a remote server database that records and tracks medication compliance.

3. The system of claim 2, wherein the patient information comprises a plurality of biometric profiles, each biometric profile corresponding to a particular patient of the plurality of patients.

4. The system of claim 3, wherein the input device is a biometric security device and the identification input is a fingerprint or other biometric identifier and wherein to verify that the particular patient is authorized to access the dispensing device comprises comparing the fingerprint or the other biometric identifier to the plurality of biometric profiles to determine a match.

5. The system of claim 1, wherein to provide access to the dispensing device comprises dispensing medication according to the prescribed schedule corresponding to the patient.

6. The system of claim 1, wherein the processor is further configured to:
generate a dispensing transaction based on the dispensed medication; and
when the medication is not dispensed as scheduled, record an entry in the remote server database to track patient medication compliance.

7. The system of claim 1, wherein the at least one processor provides access to the dispensing device by unlocking at least one of the plurality of locked compartments for dispensing medication when the patient is verified.

8. A method for dispensing medication comprising:
receiving, by at least one processor, identification input from an input device to verify that a patient of a plurality of patients is authorized to access a dispensing device of a portable dispensing apparatus;
in response to the verification,
obtain a first prescribed schedule from a plurality of prescribed schedules stored in a database, the first prescribed schedule corresponding to the patient, the first prescribed schedule defining personalized instructions for dispensing the medication to the patient and wherein the personalized instructions includes at least one instruction defining how frequently the patient should consume the medication;
providing, via the at least one processor, access to the dispensing device when the patient is verified based at least in part on the at least one instruction;
generating, via the at least one processor, a dispensing transaction when the medication is dispensed from the dispensing device; and
analyzing bio feedback results of the patient having taken the medication as received from the input device by reading a biometric chip implanted in the patient.

9. The method of claim 8, wherein the at least one processor is further configured to receive patient information corresponding to the plurality of patients.

10. The method of claim 9, wherein the patient information comprises a plurality of biometric profiles, each biometric profile corresponding to a particular patient of the plurality of patients.

11. The method of claim 10, wherein the input device is a biometric security device and the identification input is a fingerprint, and wherein to verify the particular patient is authorized to access the dispensing device comprises comparing the fingerprint to the plurality of biometric profiles to determine a match.

12. The method of claim 8, wherein the patient information comprises a plurality of prescribed schedules, each prescribed schedule corresponding to a particular patient of the plurality of patients and wherein to provide access to the dispensing device comprises dispensing medication to the patient according to the prescribed schedule corresponding to the patient.

13. The method of claim 8, wherein the dispensing device comprises a modular cassette comprising a plurality of locked compartments for storing prescribed medication of the patient, and wherein the at least one processor provides access to the dispensing device by unlocking at least one of the plurality of locked compartments for dispensing medication when the patient is verified.

14. A system for dispensing of medication comprising:
a remote server comprising a database, the database comprising patient information for a plurality of patients; and
a dispensing apparatus in operative communication with the remote server, the dispensing apparatus including a dispensing device in operative communication with the dispensing apparatus for dispensing a medication, a biometric input device for receiving an identification input from a patient, and at least one processor to:
receive identification input from the biometric input device to verify that the patient of a plurality of patients is authorized to access the dispensing device;
in response to the verification:
obtain a first prescribed schedule from a plurality of prescribed schedules stored in the database, the first prescribed schedule corresponding to the patient, the first prescribed schedule defining personalized instructions for dispensing the medication to the patient and wherein the personalized instructions includes at least one instruction defining how frequently the patient should consume the medications;
provide access to the dispensing device when the patient is verified to be authorized access to the medication;
dispense medication from the dispensing device to the patient according to the at least one instruction; and
generate a dispensing transaction when medication is dispensed from the dispensing device; and
analyze bio feedback results of the patient having taken the medication as received from the input device by reading a biometric chip implanted in the patient.

15. The system of claim 14, wherein the at least one processor is further configured to receive the patient information corresponding to the plurality of patients.

16. The system of claim 14, wherein the patient information comprises a plurality of biometric profiles, each biometric profile corresponding to a particular patient of the plurality of patients.

17. The system of claim 16, wherein the identification input is a fingerprint and wherein to verify the particular patient is authorized to access the dispensing device comprises comparing the fingerprint to the plurality of biometric profiles to determine a match.

18. The system of claim 14, wherein to provide access to the dispensing device comprises dispensing medication to the patient according to the prescribed schedule corresponding to the patient.

19. The system of claim 14, the at least one processor provides access to the dispensing device by unlocking at least one of a plurality of locked compartments of the modular dispensing cassette for dispensing medication when the patient is verified.

20. The system of claim 14, wherein the dispensing device comprises a plurality of bubbles disposed on the top side of the dispensing device for storing prescribed medication of the patient and wherein the at least one processor provides access to the dispensing device by unlocking at least one of the plurality of bubbles for dispensing medication when the patient is verified.

* * * * *